United States Patent

Cerwin et al.

[11] Patent Number: 4,483,437
[45] Date of Patent: Nov. 20, 1984

[54] SUTURE RETAINER

[75] Inventors: Robert J. Cerwin, Pittstown; Richard D. Marziaz, Highbridge, both of N.J.

[73] Assignee: Ethicon, Inc., Somerville, N.J.

[21] Appl. No.: 524,264

[22] Filed: Aug. 18, 1983

Related U.S. Application Data

[63] Continuation-in-part of Ser. No. 506,570, Jun. 22, 1983, abandoned, which is a continuation of Ser. No. 273,804, Jun. 15, 1981, abandoned.

[51] Int. Cl.³ .............................................. A61B 17/00
[52] U.S. Cl. .................................. 206/63.3; 206/363; 206/438
[58] Field of Search ...................... 206/63.3, 227, 363, 206/380, 381, 382, 388, 438, 476, 488, 489, 491, 492; 229/27, 70

[56] References Cited

U.S. PATENT DOCUMENTS

| | | | |
|---|---|---|---|
| 3,857,484 | 12/1974 | Thyen | 206/227 |
| 3,876,068 | 4/1975 | Sonnino | 206/227 |
| 4,034,850 | 7/1977 | Mandel et al. | 206/63.3 |
| 4,063,638 | 12/1977 | Marwood | 206/63.3 |
| 4,089,409 | 5/1978 | Cerwin | 206/63.3 |
| 4,249,656 | 2/1981 | Cerwin et al. | 206/63.3 |
| 4,253,563 | 3/1981 | Komarnycky | 206/63.3 |

*Primary Examiner*—Joseph Man-fu Moy
*Assistant Examiner*—David Fidei
*Attorney, Agent, or Firm*—Robert L. Minier

[57] ABSTRACT

A suture retainer for retaining a wound suture and substantially preventing the degradation by, e.g., heat or light of suture materials retained therein during subsequent handling and packaging, including during subsequent foil sealing of the suture package by completely encasing the suture materials within the retainer.

15 Claims, 10 Drawing Figures

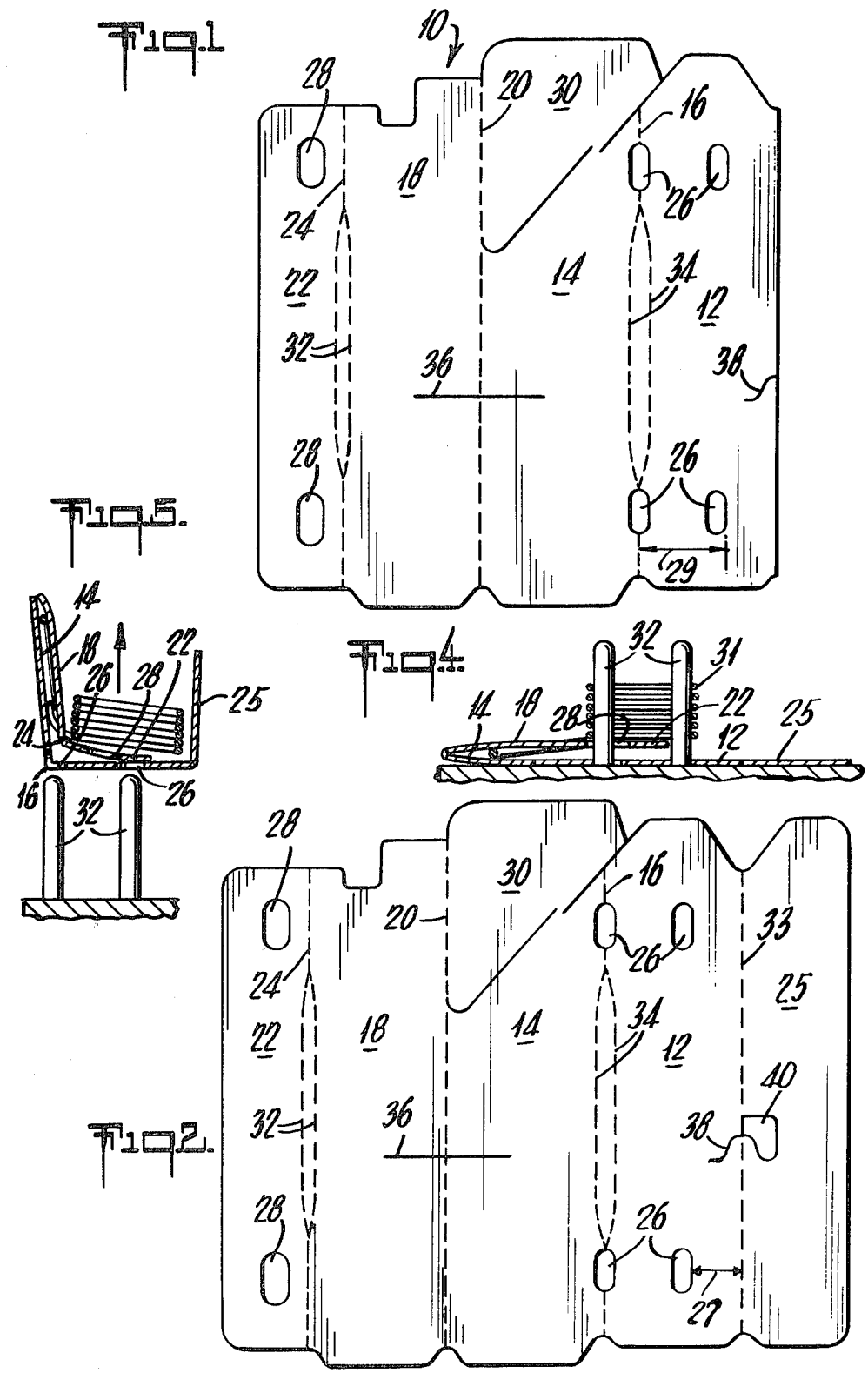

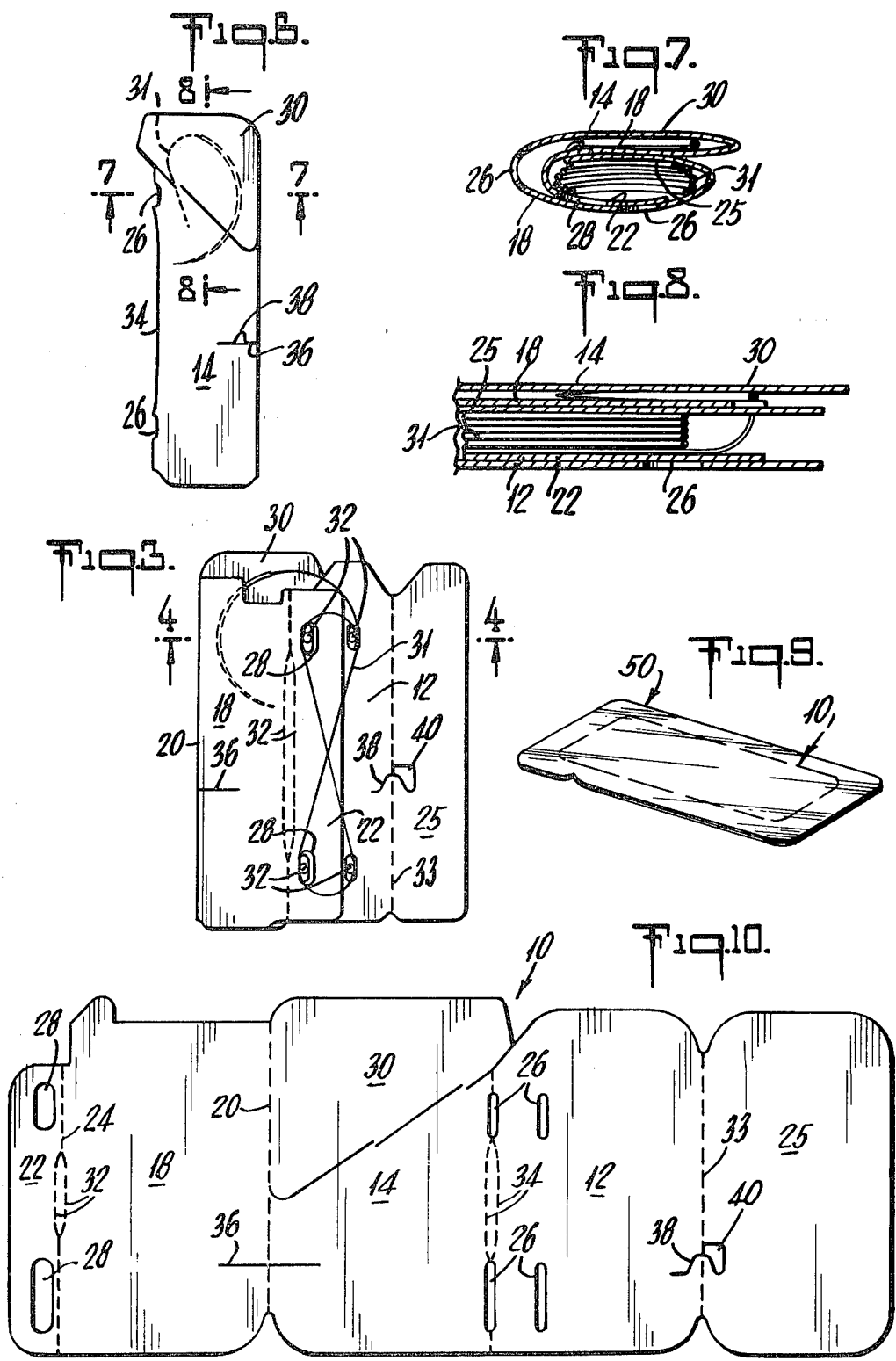

SUTURE RETAINER

REFERENCES

The present application is a continuation in part application of patent application Ser. No. 506570, filed 6/22/83, which in turn is a continuation application of patent application Ser. No. 273,804, filed June 15, 1981 both now abandoned.

In the past, suture retainers in many configurations have been provided to aid in the handling of suture material during sterilization and packaging, and/or to retain the suture in a specific configuration to facilitate dispensing of the suture from the suture package. Sutures within such retainers are sterilized and further packaged in a heat sealed outer package which maintains the suture sterility. U.S. Pat. Nos. 3,939,969 and 4,249,656 disclose suture retainers which aid in the handling, sterilization, and dispensing of the sutures contained therein, and which may be contained in a heat sealed outer package.

Suture retainers, as shown in U.S. Pat. Nos. 4,249,656 and 3,444,994 often are provided with holes or openings to receive suture winding pins so that the suture may be wound "within" the retainer. In the past, suture material secured within a retainer with pinholes remained exposed to the environment through the pinholes and was subject to degradation from environmental conditions, e.g., heat, light, and humidity, and specifically the heat in the heat sealing process often used to complete the sterile suture package.

SUMMARY OF THE INVENTION

The present invention provides a multi-panel suture retainer having holes and openings therein for receiving suture winding pins, which in its folded configuration completely encases a suture retained therein, protecting the suture material from degradation due to exposure to the environment during further processing and packaging steps.

The suture retainer has a number of substantially parallel fold lines defining panels therebetween. The suture retainer comprises in series; a suture winding panel, a first connector panel, a second connector panel and a sliding panel.

The suture winding panel has at least two suture winding pinholes each hole being spaced from the edge of the suture panel a distance equal to at least the width of the respective pinhole.

The first connector panel is connected to the suture winding panel and along a fold line. The first connector panel has a width equal to at least the distance from the fold line to the furthest edge of the furthest pinhole in the suture winding panel.

The second connector panel is connected to the first connector panel along a first fold line, and has a width equal to the width of the first connector panel minus at least one-half the width of the largest pinhole.

The sliding panel is connected to the second connector panel along a second fold line and had a width less than the width of the second connector panel. The sliding panel has openings placed therein such that when the second connector panel and the sliding panel are folded about the first fold line and overlie the first connector panel and the suture winding panel, openings are provided in the sliding panel wherever the sliding panel overlies a pinhole. The openings are of limited dimension such that when second connector panel and the first connector panel are folded about the second fold line and the fold line, respectively, the sliding panel is moved across the suture winding panel and the openings are displaced from the pinholes.

In a preferred embodiment, the retainer has a suture covering panel connected to the suture winding panel, opposite the first connector panel, along a third fold line. In another preferred embodiment at least one pinhole is located along the fold line.

In a still preferred embodiment, the suture retainer of the present invention may be locked in its folded configuration.

In another preferred embodiment, the suture retainer of the present invention may be provided with gussets between the panels, forming a suture retaining and dispensing channel.

In still another embodiment of the suture retainer of the present invention, at least one panel of the suture retainer may be provided with a detachable portion such that separation of the detachable portion exposes an end of a suture within the suture retainer; and said detachable portion may optionally be connected with an outer sealed envelope for said retainer such that a pulling force exerted on the outer envelope to open the envelope, simultaneously exerts a force on the connected detachable portion, separating the detachable portion and exposing an end of a suture within the retainer.

DESCRIPTION OF THE DRAWINGS

FIG. 1 is a plan view of one embodiment of the suture retainer of the present invention.

FIG. 2 is a plan view of another embodiment of the suture retainer of the present invention.

FIG. 3 is a plan view of the partially folded suture retainer of FIG. 1 disposed on the suture winding pins.

FIG. 4 is a cross-sectional view of the suture retainer and winding pins of FIG. 2.

FIG. 5 is a cross-sectional view of the suture retainer of FIG. 4 as it is lifted off the winding pins.

FIG. 6 is a plan view of the completely folded, locked suture retainer package of the present invention.

FIG. 7 is a cross-sectional view of the suture retainer of FIG. 5 taken along line 7—7.

FIG. 8 is a cross-sectional view of the suture retainer of FIG. 5 taken along line 8—8.

FIG. 9 is a perspective view of a suture package containing the suture retainer of the present invention.

FIG. 10 is a plan view of another embodiment of the suture retainer of the present invention.

DETAILED DESCRIPTION OF THE DRAWINGS

In the various embodiments of the suture retainer of the present invention shown in the drawings, comprising at least four panels connected along substantially parallel fold lines, similar features of the various embodiments are designated by the same number throughout the drawings. The term "suture" when used in this application relates to both a needled or unneedled strand of suture material.

The retainer 10 FIG. 1 comprises a suture winding panel 12, a first connector panel 14 connected to said suture winding panel along a fold line 16, a second connector panel 18 connected to said first connector panel along a first fold line 20, and a sliding panel 22 connected to said second connector panel along a second fold line 24. The suture winding panel is provided with at least two, and preferably four, holes 26 which may be used to mount the retainer on suture winding pins 32 as shown in FIGS. 3-5.

In a preferred embodiment shown in FIG. 2, the suture retainer may include a suture cover panel 25 connected to said suture winding panel along a third fold line 33. In this preferred embodiment each pinhole is spaced a distance 27 from the third fold line equal to at least the width of the respective pinhole. In a still preferred embodiment, at least one of the pinholes is located along the fold line.

As shown in FIG. 1, the widths of the panels, and pinholes, and distances of the suture retainers of the present invention are measured perpendicular to the fold lines.

The first connector panel 14 has a width of at least the distance 29 from the fold line to the furthest edge of the furthest pinhole, and the second connector panel 18 has a width equal to that of the first connector panel minus at least one-half the width of the largest pinhole, and in this embodiment as shown in the drawing the reduction in width is approximately equal to the width of the pinhole.

In use, the suture retainer is folded about the first fold line 20 as shown in FIG. 3 prior to winding the suture, with the second connector panel 18 and the sliding panel 22 overlying the first connector panel 14 and the suture winding panel 12. One end of the suture is preferably placed against the first connector panel prior to the folding of the retainer about the first fold line. Openings 28 are provided in the sliding panel wherever the sliding panel overlies a pinhole.

When the retainer is displaced from suture winding pins as shown in FIG. 5, and the first and second connector panels are folded about the fold line 16 and the second fold line 24, respectively, the second connector panel pushes the sliding panel across the suture winding panel, displacing the openings in the sliding panel from the pinholes. As shown in FIG. 5, in the preferred embodiment having a suture cover panel, the suture cover panel is folded along the third fold line 33 and atop the suture as the suture retainer is displaced from the suture winding pins. In the full folded configuration as shown in FIG. 6 and in cross-section in FIG. 7, the openings 28 in the sliding panel are displaced from the holes 26 in the suture winding panel and the suture is enclosed within the retainer. When a preferred embodiment having a suture cover panel is in its folded configuration, the suture cover panel 25 immediately overlies the suture 31 as shown in FIG. 7 and the second connector panel 18 overlies the suture cover panel. When the embodiment of FIG. 1 is in its folded configuration the second connector panel 18 immediately overlies the suture. As shown in FIG. 8, the first connector panel 14 overlies the second connector panel 18 with one end of the suture and a needle, if any, therebetween.

FIG. 9 illustrates in outer sealed package for the suture retainer of the present invention. Suture material encased within the fully folded retainer is protected from the environment, e.g., from heat, light or humidity during further processing, handling, and packaging, for instance in the heat sealing of the retainer within an envelope package such as that shown in FIG. 9. FIG. 10 illustrates another embodiment of the suture retainer of FIG. 1 wherein the size and proportion of individual panels, holes, and openings varies from the embodiment illustrated in FIG. 2 but the relative widths of which are in accordance with the present invention.

In its various preferred embodiments, the first connector panel of the suture retainer of the present invention may be provided with a terminal detachable section 30 as disclosed in U.S. Pat. No. 3,939,969, which is incorporated herein by reference, which detachable section may be intimately connected with a tearable outer envelope such as shown in FIG. 9 so that the tearing force on the outer envelope brings about a separation of the detachable section, exposing a suture end mounted on the detachable section.

The retainer may also be provided with gussets 32 and 34 in the second fold line and the fold line, respectively, forming a channel through which a suture may be drawn when removing the suture from the retainer, as shown in U.S. Pat. No. 4,249,656, also incorporated by reference herein.

In addition, the suture retainer may include locking means comprising a slot 36 bridging the first fold line and a tab 38 formed in the edge of the suture winding panel opposite the first connector panel whereby when said retainer is in its folded configuration, the tab engages the slot in a locking relationship as shown in FIG. 6. In the embodiment shown in FIG. 2, the tab may bridge the third fold line and a cut-out portion 40 may be provided only in the suture cover panel as distinguished from the cut-out defining locking tabs such as that shown at 23 in U.S. Pat. No. 4,249,656; as it is an object of the present invention to completely encase suture material contained within the retainer.

It will be understood by those skilled in the art that variations and modifications of the specific embodiments described above may be employed without departing from the spirit and scope of the invention as defined in the appended claims.

We claim:

1. A suture retainer having
a number of substantially parallel fold lines defining panels therebetween, said suture, retainer comprising:
   a suture winding panel,
   a first connector panel connected thereto along a fold line,
   at least two suture winding pinholes in said suture winding panel, each hole being spaced from the edge of the suture panel a distance equal to at least the width of the respective pinhole,
   said first connector panel having a width equal to at least the distance from the fold line to the furthest edge of the furthest pinhole in the suture winding panel,
   a second connector panel connected to said first connector panel along a first fold line, said second connector panel having a width equal to the width of the first connector panel minus one-half of the width of the largest pinhole, and
   a sliding panel connected to said second connector panel along a second fold line and having a width less than the width of the second connector panel and having openings placed therein such that when the second connector panel and the sliding panel are folded about the first fold line and overlie the first connector panel and the suture winding panel, openings are provided in the sliding panel wherever the sliding panel overlies a pinhole, said openings being of limited dimension such that when second connector panel and the first connector panel are folded about the second fold line and the fold line, respectively, the sliding panel is moved across the suture winding panel and the openings are displaced from the pinholes.

2. A suture retainer as in claim 1, having a suture covering panel connected to the suture winding panel at the opposite side of said first connector panel, along a third fold line.

3. A folded suture retainer as in claim 2 containing a suture, said second connector panel and said sliding panel being folded about the first fold line and overlies the first connector panel and the suture winding panel, said suture being placed upon the suture winding panel and the overlying sliding panel, and the first connector panel and the second connector panel being folded along the second fold line and the fold line, respectively, and overlying said suture.

4. A folded suture retainer as in claim 2 containing a suture, said second connector panel and said sliding panel being folded about the first fold line and overlies the first connector panel and the suture winding panel, said suture being placed upon the suture winding panel and the overlying sliding panel, the suture covering panel being folded along the third fold line and overlying said suture, and the first connector panel and the second connector panel being folded along the second fold line and the fold line respectively.

5. A suture retainer as in claim 1 or 2 whereifn the fold line includes a gusset over a substantial portion thereof.

6. A suture retainer as in claim 5 wherein the second fold line includes a gusset.

7. A suture retainer as in claim 1 or 2 wherein at least one pinhole is located along the fold line.

8. A suture retainer as in claim 1, having a locking means comprising a slot bridging said first fold line and a tab formed in the edge of the suture winding panel opposite the first connector panel whereby when said retainer is in its folded configuration the tab engages the slot in a locking relationship.

9. A suture retainer as in claim 2 having a locking means comprising a slot bridging the first fold line and a tab bridging the third fold line with a cut-out in the suture cover panel only.

10. A suture retainer having
    a number of substantially parallel fold lines defining panels therebetween, said suture retainer comprising:
    a suture winding panel,
    a first connector panel connected therein along a fold line,
    at least two suture winding pinholes in said suture winding panel, each hole being spaced from the edge of the suture panel a distance equal to at least the width of the respective pinhole,
    said first connector panel having a width equal to at least the distance from the fold line to the furthest edge of the furthest pinhole in the suture winding panel,
    a second connector panel connected to said first connector panel along a first fold line, said second connector panel having a width equal to the width of the first connector panel minus at least one-half the width of the largest pinhole, and
    a sliding panel connected to said second connector panel along a second fold line and having a width less than the width of the second connector panel and having openings placed therein such that when the second connector panel and the sliding panel are folded about the first fold line and overlie the first connector panel and the suture winding panel, openings are provided in the sliding panel wherever the sliding panel overlies a pinhole, said openings being of limited dimension such that when second connector panel and the first connector panel are folded about the second fold line and the fold line, respectively, the sliding panel is moved across the suture winding panel and the openings are displaced from the pinholes.

11. A suture retainer as in claim 10, having a suture covering panel connected to the suture winding panel at the opposite side of said first connector panel, along a third fold line.

12. A folded suture retainer as in claim 11 containing a suture, said second connector panel and said sliding panel being folded about the first fold line and overlies the first connector panel and the suture winding panel, said suture being placed upon the suture winding panel and the overlying sliding panel, the suture covering panel being folded along the third fold line and overlying said suture, and the first connector panel and the second connector panel being folded along the second fold line, respectively.

13. A suture retainer as in claims 10 or 11 wherein the fold line includes a gusset over a substantial portion thereof.

14. A suture retainer as in claim 10 or 11 wherein at least one pinhole is located along the fold line.

15. A suture retainer as in claim 10, having a locking means comprising a slot bridging said first fold line and a tab formed in the edge of the suture winding panel opposite the first connector panel whereby when said retainer is in its folded configuration the tab engages the slot in a locking relationship.

* * * * *